United States Patent [19]

Gerwick et al.

[11] Patent Number: 5,508,026

[45] Date of Patent: Apr. 16, 1996

[54] INDOLE ALKALOIDS USEFUL AS UV PROTECTIVE AND ANTI-INFLAMMATORY AGENTS

[75] Inventors: William H. Gerwick, Corvallis; Richard Castenholz, Elmira, both of Oreg.; Ferran Garcia-Pichel, Breman, Germany; Philip J. Proteau, Murray, Utah

[73] Assignee: The Regents Of The University Of California, Oakland, Calif.

[21] Appl. No.: 503,448

[22] Filed: Jul. 17, 1995

Related U.S. Application Data

[62] Division of Ser. No. 297,022, Aug. 29, 1994, Pat. No. 5,461,070.

[51] Int. Cl.$^6$ .................... A61K 31/40; C07D 209/94
[52] U.S. Cl. .................... 424/59; 514/411; 548/439
[58] Field of Search ................ 548/439; 424/59; 514/411

[56] References Cited

PUBLICATIONS

P. J. Proteau et al, Experientia, vol. 49 (1993) pp. 825–829.

*Primary Examiner*—Robert W. Ramsuer
*Attorney, Agent, or Firm*—Poms, Smith, Lande & Rose

[57] ABSTRACT

Indole alkaloid compounds having the formula

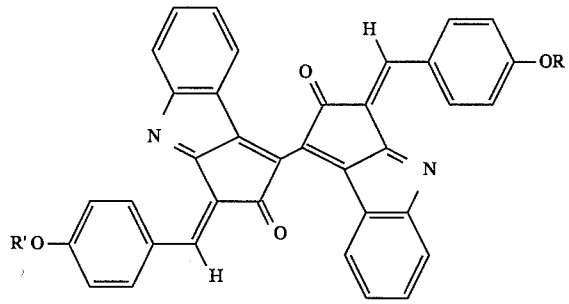

where R and R' are H, an alkyl group having up to 5 carbon atoms or —CO—$(CH_2)_n$—$CH_3$ where n=0 to 16. The indole alkaloid compounds and their reduction products are useful as both UV protective and anti-inflammatory agents.

5 Claims, No Drawings

INDOLE ALKALOIDS USEFUL AS UV PROTECTIVE AND ANTI-INFLAMMATORY AGENTS

This invention was made with Government support under Grant No. R/MP-52 NA-36-RG-0537, awarded by the National Oceanic & Atmospheric Administration. The Government has certain rights in this invention.

This is a divisional of application Ser. No. 08/297,022 filed on Aug. 29, 1994 now U.S. Pat. No. 5,461,070.

BACKGROUND OF THE INVENTION

1. Field of the Invention

The present invention relates generally to compounds which have more than one pharmaceutically desirable activity. More particularly, the present invention is directed to a newly isolated indole alkaloid compound and analogs thereof which have been found to be effective anti-inflammatory agents while also being useful as ultraviolet radiation absorbers, i.e. UV protective agents.

2. Description of Related Art

A yellow-green pigment was first isolated from sheathed cyanobacteria in the late 1870's. Although the pigment included a complex mixture of unidentified compounds, the single term "scytonemin" was introduced to identify the pigment. Since its initial discovery, scytonemin has been isolated and identified in more than 30 species of sheathed cyanobacteria. These sheathed bacteria which contain scytonemin have been found in diverse geographic regions wherever exposure to strong solar irradiance occurs. These regions have included freshwater, terrestrial and marine habitats.

An important characteristic of the scytonemin pigment is its ability to absorb ultra-violet (UV) radiation. Sheathed cyanobacteria or similar ancestral forms occur commonly as microfossils in strata of biogenic origin from the Proterozoic period and even earlier. Since UV fluxes were considerably higher then than now, it is likely that development of scytonemin for its UV-screening properties was important to the evolution of cyanobacteria. The scytonemin pigment absorbs most strongly in the UV-A spectral region. There is also significant absorbance in the UV-B region.

Although scytonemin pigment has been known as a UV absorber for many years, the various complex group or groups of compounds which are present in the pigment have not been completely isolated or identified. Accordingly, the specific ingredient or ingredients in scytonemin pigment which provide it with such strong UV absorbing properties have remained unknown.

SUMMARY OF THE INVENTION

In accordance with the present invention, it was discovered that one of the compounds present in scytonemin pigment is an indole alkaloid which not only is a strong UV absorber, but also exhibits strong activity as an anti-inflammation agent. The purified indole alkaloid, along with synthetically derived analogs, may be used alone or in combination with a pharmaceutically acceptable carrier to treat inflammation while at the same time providing UV protection.

Indole alkaloid compounds in accordance with the present invention have the formula

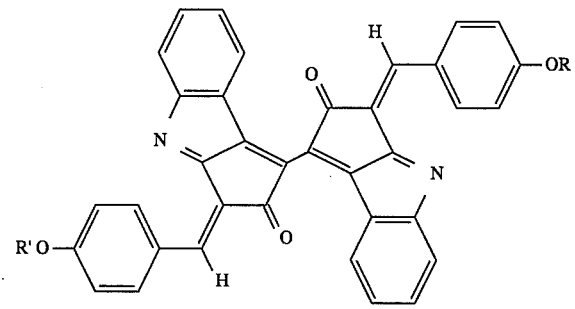

where R and R' are H, an alkyl group having up to 5 carbon atoms or $-CO-(CH_2)_n-CH_3$ where n=0 to 16. The compound where R and R' are H may be isolated and purified from naturally occurring scytonemin pigment. Ether analogs where R and R' are alkyl groups having up to 5 carbon atoms may be prepared from the naturally occurring dihydroxy indole alkaloid compound using conventional synthetic pathways. The diacetate analogs may also be prepared using well-known pathways for preparing acetate analogs from the naturally occurring dihydroxy indole alkaloid compound.

The indole alkaloid compounds in accordance with the present invention exhibit strong UV absorption which makes them well-suited for use as a general UV protective agent. In addition, it was discovered that these indole alkaloids are effective anti-inflammation agents which demonstrate high anti-inflammatory activity when subjected to standard anti-inflammatory test protocols. As a result, the compounds of the present invention may advantageously be used to treat skin inflammation while at the same time functioning as a UV protective agent.

The above discussed and many other attendant features of the present invention will become better understood by reference to the following detailed description.

DETAILED DESCRIPTION OF THE INVENTION

The indole alkaloid compounds in accordance with the present invention have the formula

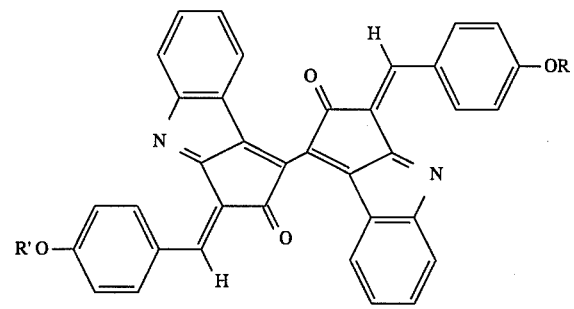

where R and R' are H, an alkyl group having up to 5 carbon atoms or $-CO-(CH_2)_n-CH_3$ where n=0 to 16. The present invention also covers the reduced form of this compound which has the formula

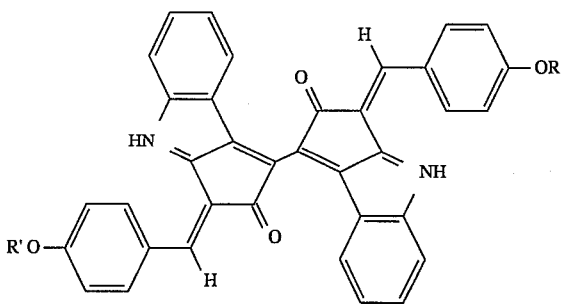

where R and R' are H, an alkyl group having up to 5 carbon atoms or —CO—$(CH_2)_n$—$CH_3$ where n=0 to 16.

The compound of the present invention where R and R' are both H (Compound 1) can be isolated and purified from naturally occurring scytonemin pigment using conventional separation and purification procedures. The isolation and characterization of Compound 1 is set forth in P. J. Proteau et al., "The structure of scytonemin, an ultraviolet sunscreen pigment from the sheaths of cyanobacteria," *Experientia* 49 (1993), pages 825 to 829.

Once having obtained the Compound 1, the ether and diacetate analogs as defined in the above formula may be prepared according to conventional procedures for forming diether and diacetate derivatives. Acetylation was accomplished generally following the procedure detailed in Gerwick, W. H. and Fenical, W., "Ichthyotoxic and cytotoxic metabolites of the tropical brown alga *Stypopodium zonale* (lamouroux) Papenfuss," *J. Org. Chem.* 1981, 46, 22–27, except that the reaction was quenched with MeOH and the excess reagents and solvents were removed in vacuo.

Metylation was accomplished generally following the method of Stoochnoff, B. A. and Benoiton, N. L., "The methylation of some phenols and alcohols with sodium hydride/methyl iodide in tetrahydrofuran at room temperature," *Tetrahedron Lett.* 1973, 21–24, except that anhydrous $K_2CO_3$ (potassium carbonate) was used instead of sodium hydride as the base.

Preferred exemplary compounds are the dimethyl ether where R and R' are methyl (Compound 2) and the diacetate where R and R' are —CO—$(CH_2)_n$—$CH_3$ and n=0 (Compound 3). In addition, if desired, additional analogs may be prepared wherein one or more halogen groups are substituted on the phenyl rings adjacent to the —OR or OR' groups.

The indole alkaloid compounds in accordance with the present invention are useful for treating inflammation. The compounds may be used in the same manner as conventional anti-inflammatory agents indomethacin, hydrocortisone, naprocin and other non-steroidal anti-inflammatory agents. The compounds are effective for both topical application and in vivo use. When used for topical application, the compounds function both as a UV protective agent and anti-inflammation agent.

Pharmaceutical compositions which contain the indole alkaloids in accordance with the present invention are useful in the treatment of rheumatoid arthritis, osteoarthritis, rheumatic carditis, collagen and/or auto-immune diseases such as myasthenia gravis, allergic diseases, bronchial asthma and ocular and skin inflammatory diseases such as poison ivy. The compositions are also useful in treating proliferative diseases such as psoriasis.

The compositions are also useful as adjuvant therapy associated with organ and tissue transplants and any neurological disease involving metabolism of nervous tissue phospholipid such as multiple sclerosis. The compositions may also be used to treat secondary inflammation resulting from septic shock and reprefusion injury associated with coronary by-pass surgery and other intra arterial surgical procedures. Because of their selective antagonism of chemical irritation (i.e., PMA inflammation) the compounds can be useful in the treatment of insect bites, bee, wasp stings, snake bites or any venom in which a major constituent is the enzyme phospholipase $A_2$.

The compounds are also potent UV absorbers which absorb strongly in the spectral region from 250 to 425 nm. The compounds absorb radiation most strongly in the UV-A-violet-blue region (325–425 nm). The compounds exhibit lesser degrees of absorption in the UV-C (250 nm) and UV-B (280–320 nm) ranges.

The indole alkaloid compounds in accordance with the present invention are administered to mammals including humans in an effective amount on the order of 1 to 100 mg per day per kilogram of body weight in divided or multiple forms. The drug may be administered orally, parenterally, topically or by other standard administration routes. For topical administration a 0.5 to 10% by weight solution of the compound in a suitable emulsion is preferred. Suitable pharmaceutical carriers for topical administration include micelles, cottonseed oil, linseed oil with polymer binding agents, and alcohol based emulsions. Other conventional emulsions used for topical administration may be used. This level of dosage for topical administration provides both anti-inflammation efficacy and UV protection. For oral administration, the dosage form may be by tablet containing normal acceptable additives, excipients, etc. The parenteral form contains typical aqueous intravenous solution ingredients such as propylene glycol dextrose and physiological saline or other suitable lipid solubilizing carrier.

An exemplary procedure for isolating and purifying Compound 1 is as follows:

Scytonemin pigment was obtained from *Stigonema sp.* from Waldo Lake, Oregon, from *Scytonema sp.* from Curacao, Netherlands Antilles and *Lyngbya sp.* from Huahine, French Polynesia. The scytonemin pigment was extracted to yield a crusty green solid. The extraction procedure was carried out as described by Garcia-Pichel, F. et al., *Phycol.* 27 (1991) 395. The procedure for extraction was as detailed in Garcia-Pichel, which involves the following: the fresh alga was repetitively extracted with warm EtOAc and MeOH. These combined extracts were diluted with distilled water (50% vol/vol), cooled to 4° C. or lower for 10–30 minutes, and then the insoluble material filtered through Whatman GF/F or GF/C filters to give a crude scytonemin preparation. Carotenoids and chlorophyll derivatives contaminating this preparation could be removed by washing the filter with petroleum ether and methanol-water (1:4).

Further extractions using acetone/water (5:2), THF/EtOH (5:1) and EtOAc resulted in the isolation of small, disordered needle clusters of essentially pure Compound 1 (>99% by thin layer chromatographic analysis). These crystals of Compound 1 were stable and had a melting point of greater than 325° C.

Compound 1 shows a variable degree of solubility in N,N-dimethylformamide (DMF), pyridine or tetrahydrofuran (THF). Simple chemical reduction of Compound 1 with a variety of mild reducing agents (e.g., ascorbic acid) yields a bright red pigment with slightly improved solubility properties (Compound 1R). This reduction product often appears in scytonemin-containing sheaths when the cyanobacteria become buried in anoxic sediments and in microbial mat layers and when the cells are no longer viable. Compound 1 is easily reformed from Compound 1R by air oxidation on silica gel of NaIO$_4$ oxidation.

Compound 1 and its reduction product (Compound 1R) were both analyzed for C$_{36}$H$_{22}$N$_2$O$_4$ (obs M+546.1578, −0.2 mamu dev.) by high resolution fast atom bombardment mass spectrometry (HR FAB MS), and hence, appeared to possess 27 degrees of unsaturation. Compound 1, the oxidized form of the compound with 28 degrees of unsaturation, apparently undergoes a facile reduction in the mass spectrometer. $^{13}$CNMR spectroscopy of Compound 1 and Compound 1R was also carried out. Based on the above analysis, the structure of Compound 1 and Compound 1R were determined to be as set forth in the above formulas where R and R' are methyl.

The efficacy of Compound 1 and Compound 1R as anti-inflammation agents was established as follows:

Inhibition of Inflammation (Edema) of the Mouse Ear

Compounds 1 and 1R were topically applied in acetone to the inside pinnae of the ears of mice in a solution containing the edema-causing irritant, Phorbol 12-myristate 13-acetate (PMA). PMA alone (2 µg/ear) or in combination with 50 µg/ear of test compound was applied to the left ears (5 mice per treatment group) and acetone was applied to all right ears. After 3 hours, 20 minutes incubation, the mice were sacrificed, the ears removed and bores taken and weighed. Edema was measured by subtracting the weight of the right ear (acetone control) from the weight of the left ear (treated). Results are recorded as % decrease (inhibition) or % increase (potentiation) in edema relative to the PMA control group edema. The results of these tests are shown in Table 1.

TABLE 1

Inhibition of Mouse Ear Edema

| Compound | Topical Dose | Inhibition |
| --- | --- | --- |
| Compound 1 | 50 ug/ml | 89% |
| Compound 1R | 50 ug/ml | 94% |
| Ozonolysis fragment of Compound 1 | 100 ug/ml | 63% |

Dose Response Inhibition of Mouse Ear Edema

| Topical Dose | Compound 1 | Compound 1R |
| --- | --- | --- |
| 100 ug/ear | 98% | 95% |
| 50 ug/ear | 89% | 94% |
| 25 ug/ear | 90% | |
| 10 ug/ear | 44% | 49% |
| 5 ug/ear | 16% | 17% |
| 1 ug/ear | | 22% |

Arachidonic acid (AA) is an alternate edema-causing irritant which was used instead of PMA in a second study. Arachidonic acid was applied topically at 2 mg/ear in conjunction with the test compound. Arachidonic acid induced edema occurs more quickly, producing measurable edema within one hour, at which time the mice were sacrificed, the ears removed, and bores taken and weighed. The results of this study are shown in Table 2.

TABLE 2

Inhibition of AA-Induced Mouse Ear Edema

| Compound | Topical Dose | Inhibition |
| --- | --- | --- |
| Compound 1 | 100 ug/ear | 29% |
| Compound 1 | 50 ug/ear | 27% |

Bee Venom Radiometric Phospholipase A$_2$ Assay

Phosphatidylcholine dipalmitoyl (labeled and unlabeled) was used as the substrate in monomolecular form. Test compounds were preincubated with the enzyme (25 units/ 0.5 ml) for 1 hour at 41° C. The reaction was initiated by the addition of an aliquot of the drug-enzyme mixture to the substrate (0.68 µmole/0.5 ml) and allowed to continue for 15 seconds. The reaction was terminated and the hydrolysis product was extracted and measured via scintillation counting. For screening, Compound 1 (in methanol or DMSO) was added to the enzyme at a standard bench concentration of 5 mg/ml for an enzyme-incubation concentration of 80 µg/ml, and a final concentration of 0.8 µg/ml. Assays were done in triplicate and results were averaged and compared to a vehicle control rate of hydrolysis. The results of the assays are shown in Table 3.

TABLE 3

Inactivation of Bee Venom pLA2

| Compound | Final Concentration | Inactivation |
| --- | --- | --- |
| Compound 1 | 1.6 ug/ml | 39% |
| Compound 1 | 0.8 ug/ml | 30% |
| Compound 1 | 0.16 ug/ml | 27% |

Myeloperoxidase (MPO) Enzyme Assay

The neutrophil-specific marker released from primary granules, myeloperoxidase (MPO), in ear biopsies from treated and untreated mouse ears was extracted and quantitated according to a modified method of Bradley, P. O., Priebat, D. A., Christensen, R. D. and Rothstein, G., "Measurement of cutaneous inflammation estimation of neutrophil content with an enzyme marker," *J. Invest Dermatology* 78: 206–209, 1982. This enzyme is indicative of the extravasation of pro-inflammation neutrophils from blood into the skin. Ear bores from each treatment group from mouse ear edema assays were pooled and homogenized in 80 mM sodium phosphate buffer (pH 5.4) containing 0.5% hexadecyltrimethylammonium bromide in a siliconized glass test tube for 1 min. at 0° C. using a Brinkman Polytron. The mixtures were centrifuged at 10,000×g at 4° C. for 30 min. Samples (10 µl) from each group were then assayed in a 96-well microtiter plate. The assay was initiated by adding 250 µl of o-dianisi-dine/phosphate reagent (0.28 mg of dianisidine added to 1 ml of 50 mM sodium phosphate containing 0.0015 H$_2$O$_2$) to each well. After a 30 minutes incubation of 37° C., the plates were read at 450 nm on a Molecular Devices microplate reader. Diluted control biopsies were utilized to develop a standard curve. Optical density values from drug-treated groups were compared to control groups to determine % of control values of enzyme activity. The results of the assays are shown in Table 4.

TABLE 4

MPO Enzyme Activity

| Dose | Compound | % of Control |
| --- | --- | --- |
| 100 ug/ear | Compound 1 | 70% |
| 50 ug/ear | Compound 1 | 72% |
| 100 ug/ear | Compound 1R | 10% |
| 10 ug/ear | Compound 1R | 32% |
| 5 ug/ear | Compound 1R | 82% |
| 1 ug/ear | Compound 1R | 81% |

The above assays demonstrate the ability of Compound 1 and its reduction product Compound 1R to reduce inflammation when administered topically. The anti-inflammation efficacy of the two compounds is also expected to be present when they are administered orally or parenterally to treat internal inflammation. The UV absorption spectra of Compounds 1 and 1R where both measured and found to absorb strongly in the 325 to 425 nm spectral region. Accordingly, these two compounds are useful as a dual purpose pharmaceutical compound which can be used to both treat inflammation and provide UV protection. The compounds are particularly well-suited for treating individuals with skin inflammation caused by over exposure to the sun.

The methyl ether analog of Compound 1 (R and R'=methyl) was prepared as set forth in Gerwick, W. H. and Fenical, W., "Ichthyotoxic and cytotoxic metabolites of the tropical brown alga *Stypopodium zonale* (lamouroux) Papenfuss," *J. Org. Chem.* 1981, 46, 22–27. A description of the procedure was used as follows:

29.3 mg of scytonemin pigment was oven dried at 100° C. for 30 minutes, dissolved in 270 µl of tetrahydrofuran, 28 mg of $K_2CO_3$ was added and stirred. To this was added 34 µl of methyl iodide. The flask was maintained dry at room temperature for 32 hours. At this time, the excess solvents were removed in vacuo. The sample was resuspended in tetrahydrofuran (ca. 5 ml) and then filtered through Whatman #1 filter paper. Preparative TLC (10% methanol in chloroform, Kieselgel 60 Aluminum backed TLC sheets) of the tetrahydrofuran resuspended material gave a high $R_f$ band that was principally the dimethyl product of scytonemin (ca. 14 mg).

The reduced form of the methyl ether analog is prepared from the analog in the same manner as Compound 1R is prepared from Compound 1. Both the methyl ether analog and its reduction product may be used in the same manner as Compound 1 and Compound 1R to treat inflammation of tissue and provide UV protection.

The diacetate analog of Compound 1 (R and R' is —CO—$(CH_2)_n$—$CH_3$ where n=0) was prepared as follows:

To 11.4 mg of scytonemin pigment dissolved in 300 µl of pyridine was added 300 µl of acetic anhydride with stirring. The reaction was run for 20 hours at room temperature, at which time it was quenched with methanol. Solvents and spent reagents were removed in vacuo to give crusty brown solid. This was resuspended in tetrahydrofuran, filtered through Whatman #1 filter, and the resultant eluant was concentrated to give 7.8 mg of crude product. That which did not redissolve in tetrahydrofuran was found to constitute the diacetate product in greater than 90% purity (1.4 mg of product).

The reduced form of the diacetate analog is prepared from the analog in the same manner as Compound 1R is prepared from Compound 1. Both the diacetate analog and its reduction product may be used in the same manner as Compound 1 to treat inflammation of tissue and provide UV protection.

Having thus described preferred exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims. The articles and other references listed above are all hereby incorporated by reference.

What is claimed is:

1. An indole alkaloid compound having the formula

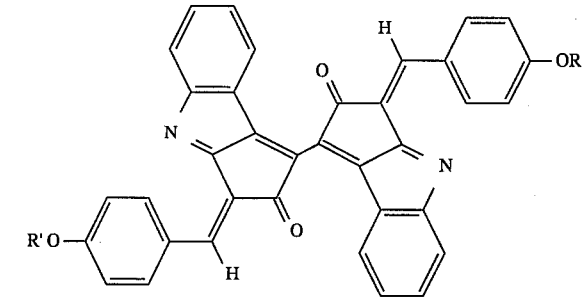

where R and R' are H.

2. A pharmaceutical preparation comprising:
an indole alkaloid compound having the formula

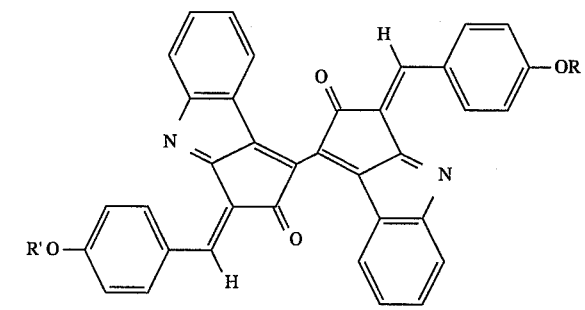

where R and R' are H; and
a pharmaceutically acceptable carrier for said compound.

3. A method for treating the skin of a mammal to provide UV protection for the skin of said mammal, said method comprising the step of administering to the skin of said mammal a UV protective amount of an indole alkaloid having the formula:

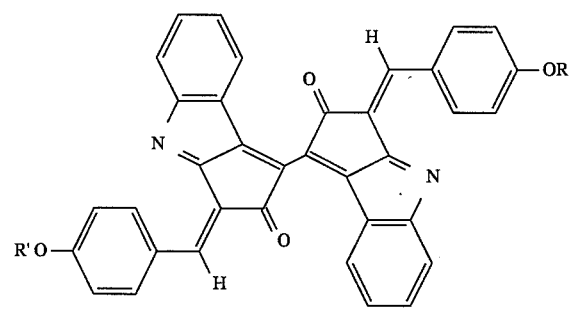

where R and R' are H.

4. A compound for use as a UV protective and/or anti-inflammation agent, said compound comprising the reduction product of an indole alkaloid having a formula according to claim 1.

5. A method for treating the skin of a mammal to provide UV protection for the skin of said mammal, said method comprising the step of administering to the skin of said mammal a UV protective amount of the reduction product of an indole alkaloid having a formula according to claim 1.

* * * * *